United States Patent [19]

Thomason et al.

[11] Patent Number: 4,817,184
[45] Date of Patent: Mar. 28, 1989

[54] ELECTRONIC INSPECTION SYSTEM AND METHODS OF INSPECTION

[75] Inventors: Robert L. Thomason, Orange County; Jack Sklansky, Newport Beach, both of Calif.

[73] Assignee: Vartec Corporation, Irvine, Calif.

[21] Appl. No.: 851,166

[22] Filed: Apr. 14, 1986

[51] Int. Cl.$^4$ .............................................. G06K 9/48
[52] U.S. Cl. ........................................... 382/8; 382/22
[58] Field of Search .................... 382/21, 22, 27, 8; 358/105

[56] References Cited

U.S. PATENT DOCUMENTS

| | | | |
|---|---|---|---|
| 3,297,993 | 1/1967 | Clapper | 382/22 |
| 3,805,239 | 4/1974 | Watanabe | 382/51 |
| 3,936,800 | 2/1976 | Ejiri et al. | 358/105 |
| 3,973,239 | 8/1976 | Kakumoto et al. | 382/50 |
| 4,074,231 | 2/1978 | Yajima et al. | 382/50 |
| 4,396,903 | 8/1983 | Habicht et al. | 382/22 |
| 4,499,598 | 2/1985 | Chittineni | 382/22 |
| 4,545,067 | 10/1985 | Juvin et al. | 382/21 |
| 4,553,260 | 11/1985 | Belt et al. | 382/22 |
| 4,561,104 | 12/1985 | Martin | 382/22 |
| 4,618,989 | 10/1986 | Tsukune et al. | 382/22 |
| 4,685,143 | 8/1987 | Choate | 382/21 |

Primary Examiner—Leo H. Boudreau
Attorney, Agent, or Firm—Blakely, Sokoloff, Taylor & Zafman

[57] ABSTRACT

An inspection system and method suitable for high speed inspection of articles having bounded surfaces are disclosed. The apparatus processes the image of the item being inspected to provide a first processed image comprising the modulus of the light intensity from the article being inspected, and a second modified image comprising, for each point, the angle of the highest light intensity gradient at that point in the image. The variability of the angle throughout the image is then determined, and the modulus and variability combined such as, by way of example, by point by point multiplication, to provide image data comprising a quantitative evaluation of the image. This data in turn may be combined into a single quantitative measure indicating the desired characteristics of the article being inspected for acceptance and rejection, or otherwise used to determine surface characteristics, locate known or unknown surface anomalies, and/or determine the size, shape, orientation, etc. of an outline or a portion thereof, as desired. The determination and use of the variability of the angle, either alone or in conjunction with the modulus highlights the boundaries of the object for emphasis or de-emphasis, as desired, as angle variability in the region of a boundary is normally very low. Also, other uses of the variability of the angle or other angle dependent information alone or with the modulus avoids the use of matrix rotations for nonoriented objects, again grossly speeding data reduction. Alternative embodiments and methods of data analysis, smoothing, clipping and shaping are disclosed.

37 Claims, 6 Drawing Sheets

1×1 CELL

2×2 CELL

3×3 CELL

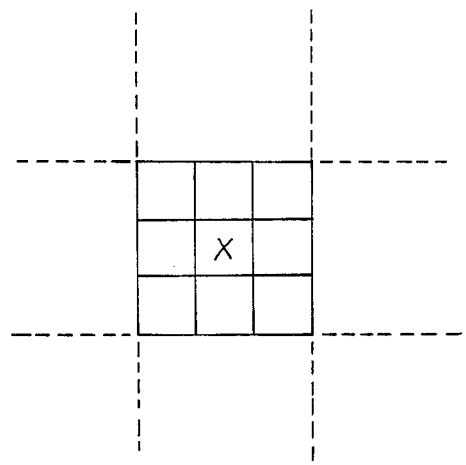
Fig. 7a
$\Delta x = R_1 + R_2 + R_3 - (L_1 + L_2 + L_3)$
Fig. 7b
$\Delta y = T_1 + T_2 + T_3 - (B_1 + B_2 + B_3)$
Fig. 7c
∠ DEFINITION
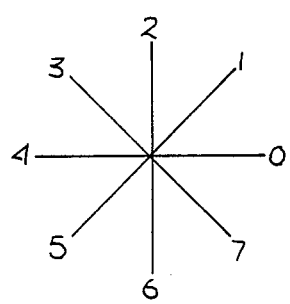
= 3 BIT BINARY
Fig. 7d

ELECTRONIC INSPECTION SYSTEM AND METHODS OF INSPECTION

BACKGROUND OF THE INVENTION

1. Field of the Invention

The present invention relates to the field of vision systems, and more particularly, to vision systems for the quantitative evaluation of an area, surface and/or the size, shape or orientation of an outline or a portion thereof.

2. Prior Art

In recent years considerable effort has been expended in developing methods and apparatus for the automatic inspection and/or quantitative evaluation of various manufactured or other things, as automatic inspection in most instances offers the possibility of substantially reducing labor costs, of eliminating human error, frequently aggravated by the monotony of many inspection tasks, and of providing greater uniformity in the inspection or evaluation results. Of particular importance to some applications of the present invention are those applications which require the evaluation of an area, and more particularly of a bounded area wherein the area is intended to be evaluated right up to the boundaries thereof, or alternatively, the location of and/or characteristics determined by the boundary (position orientation, etc. of the item).

By way of example, in some instances, such as in medical specimen analysis, a portion of an area or image is to be analyzed as representative of the entire specimen In such instances the surface being inspected or analyzed is physically larger than the portion thereof used for vision system analysis so that the edges of the image analyzed are in effect data boundaries, not object boundaries In other instances however, such as in the automatic inspection of parts in a manufacturing environment, one normally desires to inspect the surface of the part right up to the edges of the image thereof. Using light intensity gradient analysis of the image results in a very strong emphasis of the image boundaries, which in effect must be eliminated before the remaining data will be useful This can be done by finding a boundary in the data and then erasing the data corresponding to the edge by use of an algorithm which effectively bounces back and forth across the edge to isolate the data to be erased. It can also be done by scanning the object to threshold it with its background to detect and erase the edges, though both of these techniques are time consuming and generally require knowledge of the shape of the object, and if not fundamentally round, of its orientation also. While a fixed digital mask could be used to mask the image once stored in memory in digital form, such a technique would require very accurate position and orientation of the object, frequently not feasible in a real time, high speed inspection environment.

Image analysis hardware and analytical techniques which depend upon the intensity gradient across the image area do effectively distinguish regions of an area which for any reason have a light intensity which begins to deviate from the intensity of surrounding areas. In effect, the intensity gradient is the first derivative of intensity itself, which results in the emphasis of point to point changes regardless of their causes. The purpose of the present invention is to provide a method and apparatus for automatic inspection which will automatically detect, and if desired, emphasize or de-emphasize part boundaries, and which will readily facilitate data smoothing, shaping and other manipulation to result in a very high speed and reliable inspection system. As an example of a present invention system which in effect is used to de-emphasize part boundaries, an inspection system is described herein for inspecting O-rings for surface defects therein. In general, O-rings have not been inspected by prior art inspection systems because of the prominence of the ID and OD boundaries thereof, particularly in comparison to the relatively limited surface area of typical O-rings, and the flexibility of at least many O-rings, making the very accurate positioning of an O-ring so that the edges thereof may be masked within the system substantially impossible. Another example of the application of the present invention disclosed herein is the inspection of beans and the like to detect the presence of one or more stems thereon. In this case the present invention is used to emphasize the stem boundaries, with the presence of the stem being detected by detecting the presence of an image portion having adjacent edge boundaries of a separation indicative of the presence of the stem. In general, prior art inspection systems have not been able to detect the presence of stems on such food products, as the lack of orientation of the items being inspected, together with the lack of ability of prior art techniques to uniquely characterize stems no matter where located in the field of view, has left prior art techniques substantially useless for such applications. These of course are but mere examples of the ability of the present invention system to be tailored to work satisfactorily in various applications in which prior art techniques are not useful, merely by making various adjustments and parameter changes in the system and/or the manner in which the final data is analyzed and/or combined to highlight the effect being inspected for.

BRIEF SUMMARY OF THE INVENTION

An inspection system and methods suitable for high speed inspection of articles having bounded surfaces are disclosed. The apparatus processes the image of the item being inspected to provide a first processed image comprising the magnitude (modulus) of the gradient of the light intensity (gradient modulus) from the article being inspected, and a second modified image comprising, for each point, the angle of the light intensity gradient (gradient angle) at that point in the image. The variability of the gradient angle throughout the image is then determined, and the gradient modulus and variability combined such as, by way of example, by point by point multiplication, to provide image data comprising a quantitative evaluation of the image. This data in turn may be combined into a single quantitative measure indicating the desired characteristics of the article being inspected for acceptance and rejection, or otherwise used to determine surface characteristics, locate known or unknown surface anomalies, and/or determine the size, shape, orientation, etc. of an outline or a portion thereof, as desired. The determination and use of the variability of the gradient angle, either alone or in conjunction with the gradient modulus separates the boundaries of the object for emphasis or de-emphasis, as desired, since the gradient angle variability in the region of a boundary is normally very low compared to higher gradient angle variability for surface defects within the boundary. Accordingly, the use of time consuming techniques to eliminate the effect of very high light intensity gradients at the boundaries of an object being inspected characteristic of light intensity dependent image analysis systems is avoided, allowing very high speed noniterative and nontrial and error image analysis. Also, other uses of the variability of the gradient angle or other gradient angle dependent information alone or with the gradient modulus avoids the use of matrix rotations for nonoriented objects, again grossly speeding data reduction. Alternative embodiments and methods of data analysis, smoothing, clipping and shaping are disclosed.

BRIEF DESCRIPTION OF THE DRAWINGS

FIGS. 7a through 7d are diagrams illustrating the Delta X, Delta Y and gradient angle variation, and calculations for a particular cell based upon the respective neighborhood of cells.

DETAILED DESCRIPTION OF THE INVENTION

Figure 1:
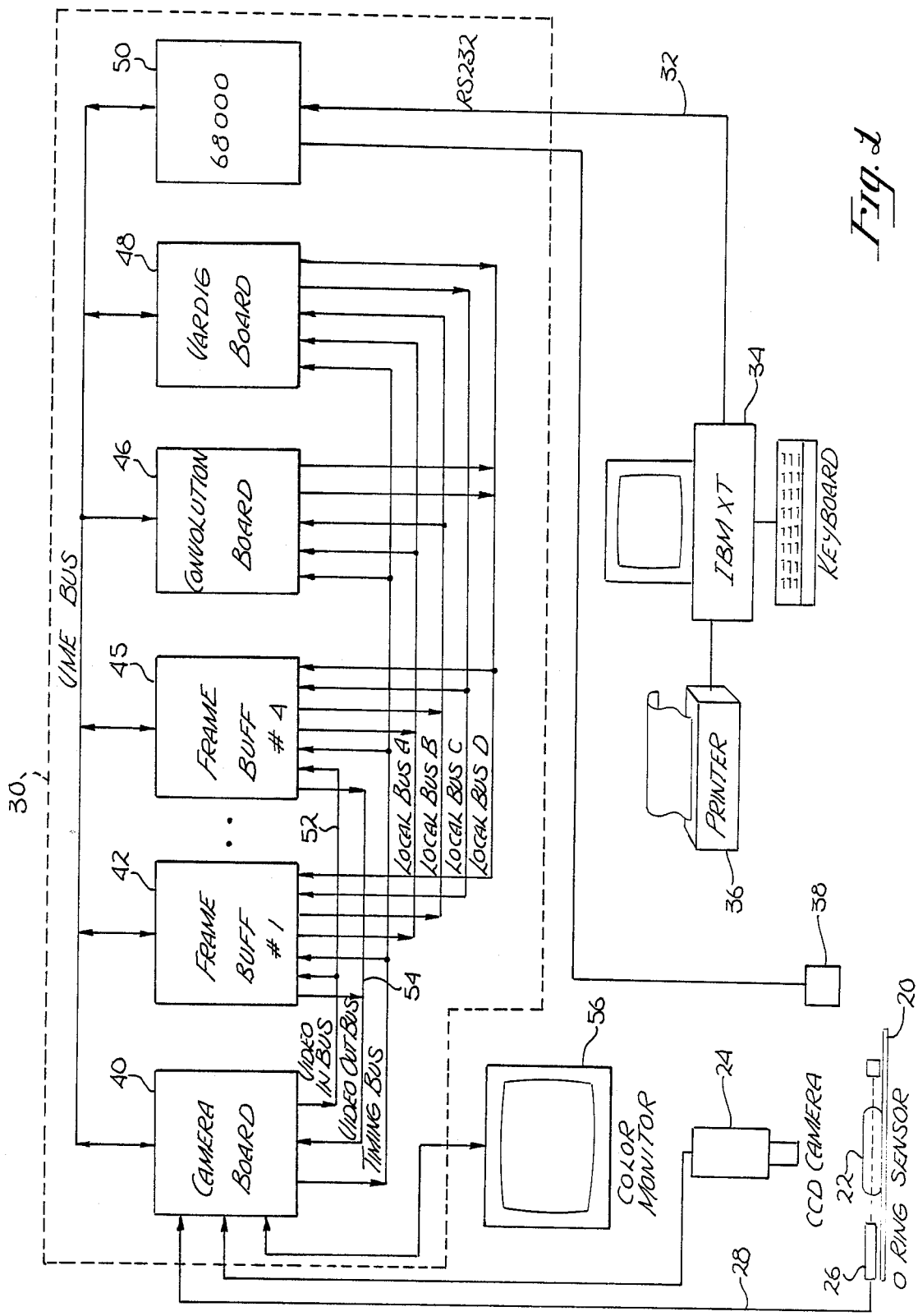
FIG. 1 is a block diagram of the preferred embodiment of the present invention.

First referring to FIG. 1, a block diagram of the system of the present invention may be seen. This figure illustrates the overall system organization in a typical inspection environment wherein the article being inspected passes the inspection camera on an appropriate transport means such as, by way of example, a conveyor, the camera image of the article is processed and an ultimate accept-reject decision is made, with the article being removed from the stream of articles upon the rejection thereof. Alternatively, good articles may be removed so that malfunction of any part of the system will result in the rejection of all articles, which of course may then be reinspected, as opposed to a malfunction causing articles which should have been rejected being mixed with articles which properly passed or would have passed inspection and being used or shipped before the malfunction was detected. For purposes of specificity in the description to follow it is assumed that the article being inspected is an O-ring seal manufactured by the molding of a suitable elastomeric material Obviously while the system is suitable for the inspection of many different manufactured and other articles, the inspection of O-rings is a good exemplary application of the invention, as O-rings are a relatively low cost, high production volume article, expensive to manually inspect on a 100% basis in comparison to the cost of the product, and which has very long and prominent inner diameter and outer diameter boundaries, particularly in comparison to the area of the surface being inspected for substantial scratches or surface depressions resulting from lack of mold filling and the like. O-rings are also a good exemplary article for inspection by the present invention in that while the article is basically circular so that theoretically a fixed masking of the data could be used in a prior art system dependent only on gradient modulus, in reality the inability to accurately position the O-rings in a high speed inspection system and their flexibility and tendency to somewhat deviate from a perfect circle make such masking impossible or very poor at Best.

As shown in FIG. 1, a transport system 20 is provided to transport O-rings 22 past a charge coupled device camera 24. An O-ring sensor 26 senses the movement of the O-ring past the camera 24 to provide a signal on line 28 to the inspection system electronics, generally located within the dashed enclosure 30, to initiate the operation of an inspection cycle. As shall be subsequently described the charge coupled device camera 24 comprises a linear array of sensors which effectively act as a raster scan to provide full two dimensional image data as the O-ring passes by. Of course also included but not shown, is a lighting system for appropriately illuminating the O-rings. The processing of the image data is done within the image processor 30, a special high speed processing system subsequently described in detail. Communication with the image processor for providing various types of mode selection and other information thereto and for providing inspection results therefrom is provided by an RS232 line 32 linking the image processor and an IBM XT computer 34, having a printer 36 connected thereto to provide a hard copy of inspection results. A reject mechanism or alternatively an accept mechanism 38 is coupled to the image processor to control the reject or accept functions.

The processing system 30 is generally comprised of five basic printed circuit board types, specifically a camera board 40, a frame buffer board (four being used, specifically frame buffers 42 through 45), a convolution board 46, a VARDIG board 48 and a 68000 processor board 50. These boards may be briefly described as follows: Camera Board The camera board 40 accepts video input from the charge coupled device 24, specifically a 512 element linear CCD scan array, and prepares this data for transfer to one of the frame buffer boards. Data preparation consists of converting the analog camera data to digital form, multiplying each pixel in the 512 pixel array by its own scale factor to correct for differences in gray shade sensitivity, translating this data via a programmable look-up table and transferring this data over a video bus 52 to one of the frame buffer boards 42 through 45. The camera board also accepts information on another video bus 54 from the frame buffers and provides the necessary look-up tables, timing and digital to analog (D/A) converters to drive a medium resolution full color display monitor 56. All camera timing, display monitor timing, frame buffer timing, and basic system operation timing is provided by the camera board. In addition, the camera board contains an interface to the 68000 Ominibyte board 50 which allows the 68000 to download the various camera board look up tables and also allows the camera board to transfer scan and frame timing signals to the 68000.

Frame Buffers

The frame buffer boards 42 through 45 each provide storage for a full 512×512×8 bit per pixel (gray shade) image. The frame buffer can receive information from the camera board 40 on the Video In Bus 52 at the camera 24 input rate of approximately 600 nanoseconds per pixel. The frame buffer can also transfer data to the camera board 40 on the Video Out bus 54 to be displayed on the display monitor 56 at a 100 nanosecond per pixel rate. Each of the frame buffers 42 through 45 can also place video data on this bus at the camera input rate if it is desired that the frame buffer simulate camera input data. Four additional byte wide buses are provided, specifically local bus A, B, C and D (sometimes referred to herein as LBA, LBB, LBC and LBD respectively). These are high speed buses which transfer data to or from the frame buffers. Local buses A and B can be driven by each of the frame buffers 42 through 45, whereas the local buses C and D are used to provide the data to the frame buffers. The local bus data rate allows the frame buffers to transfer a full frame of image data in or out of the frame buffer memory within 1/60 of a second. Scroll and pan features are provided which correct pixel delays and vertical offsets caused by external processing.

Each frame buffer is mapped into the 68000 processor memory address space, which allows the 68000 to transfer pixel data (eight bits wide) to or from the memory. The address sequence is selectable at each frame buffer, allowing data transfers to automatically sequence in either a horizontal or vertical manner.

Convolution Board

The convolution board 46 performs three separate functions, specifically image smoothing, gradient angle and gradient modulus generation, and arithmetic multiplication of a three bit data value (angle variability value) and an eight bit data value (gradient modulus). The image smoothing is a matrix operation which takes a full frame of data and within 1/60th of a second smoothes every pixel within that image. The smoothing operation replaces each pixel with an average derived by summing the original pixel value and its eight surrounding neighbors and dividing by nine. The gradient operation provides a gradient modulus and gradient angle for each pixel in a full 512×512 frame. This computation is derived for each pixel by taking it with its eight neighbors (a 3×3 cell) and first computing Delta X and Delta Y values. The Delta X value is derived by taking the difference between the sum of the right and left hand columns of pixels, the Delta Y value is computed by taking the difference of the sum of the top and bottom rows of pixels. These Delta X and Delta Y values are then processed by two trigonometric processing units to separately derive a vector magnitude and a vector angle, herein called a gradient modulus and a gradient angle.

A multiplier unit on the convolution board provides the multiplication of an eight bit value (gradient modulus) by a three bit value (angle variability value). The convolution board provides the multiplication of two full frames of image data within 1/60 of a second.

A look-up table (LUT) is also provided on the convolution board. This allows the results of any of the three operations described above to be translated by a look-up table whose values can be down loaded from the 68000. This look-up table actually consists of eight separate 256 word by eight bit look-up tables. An LUT is selected by transferring an eight bit mode control byte from the 68000 to the convolution board.

The convolution board receives data from the frame buffers on the LBA and LBB buses and transfers information to the frame buffers over the LBC and LBD buses.

VARDIG Board

The VARDIG board 48 provides four separate operations; mean angle generation, angle count computation, data translation and defective pixel table generation.

The mean angle generation is a smoothing process which takes the gradient angles (derived from the convolution board) and replaces the center pixel of a 3×3 pixel array or the upper left pixel of a 2×2 pixel array with the computed mean angle. Mean angles are computed for every pixel position in a 512×512 array within 1/60 of a second.

Figure 2:
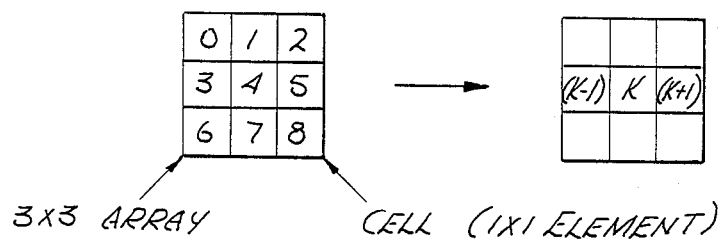
FIG. 2 is a diagram illustrating the 3×3 array or neighborhood of cells used in the preferred embodiment of the present invention, each of which cells may be a single pixel, a 2×2 pixel array or a 3×3 pixel array.
Figure 2:
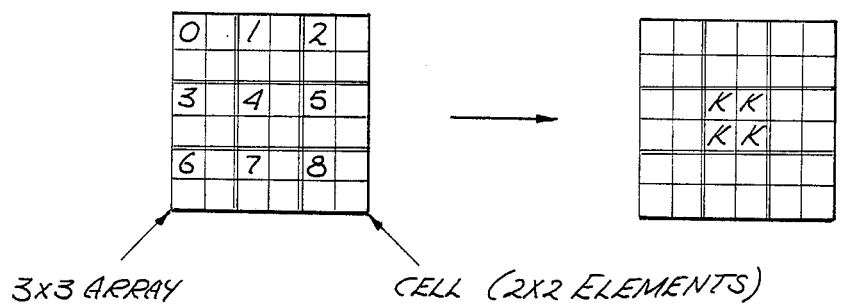
Figure 2:
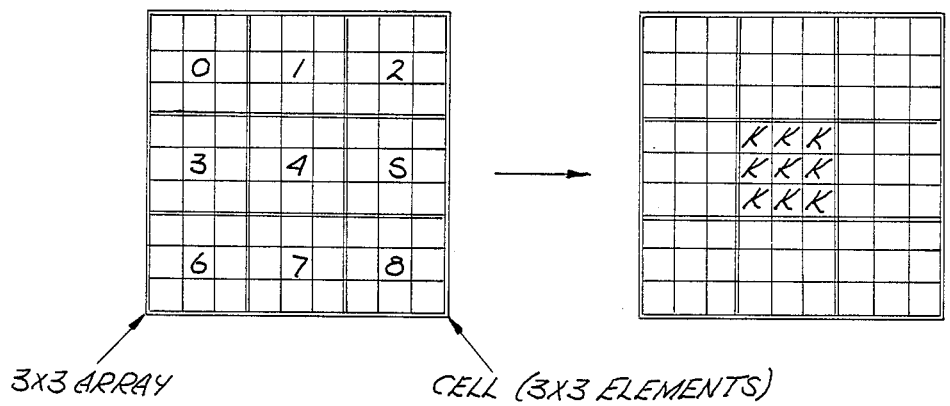

The angle count computation determines how many gradient angles (or mean gradient angles) of different directions occur within an array. There are three array configurations which can be used for the angle count. Each array consists of a 3×3 grouping of cells. This provides nine cells to be examined for the angle count computation. Three cell sizes can be selected to allow coarser or finer resolution when evaluating an image; 1×1, 2×2, or 3×3 pixels. If either a 2×2 pixel cell or a 3×3 pixel cell size is selected, the mean angles within each cell are first generated as described in the last paragraph. When a 2×2 pixel cell is used, the angle value in the upper left pixel of the cell is then selected from each of the 9 cells; if a 3×3 pixel cell is used, the angle value located in the center pixel is selected from each of the 9 cells. When a 2×2 or 3×3 pixel cell is used, the resulting angle count is stored in all pixels of the center cell. The next array analyzed will be displaced by one cell (1, 2, or 3 pixels for a 1×1, 2×2, or 3×3 pixel cell, respectively). FIG. 2 illustrates these three cell structures.

The data translation function provides look-up table translation for an image held in a frame buffer. A look-up table structure identical to that described for the convolution board is provided on the VARDIG board. This allows the results of a mean angle or angle count operation to be clipped, thresholded, scaled, or otherwise translated. Eight 256×8 look-up tables are provided on the VARDIG board which can be loaded under program control from the 68000. A look-up table is selected by transferring a mode byte from the 68000 to the VARDIG board.

The defective pixel table generator provides a summary plot of the pixels which have been determined to be defective through the VARDIG and gradient computations. The table is 256 bytes long. Each byte represents the number of defective pixels which occur on two adjacent scan lines. Although two adjacent scan lines contain 1024 pixels, it is assumed that no more than 255 will be defective. In any case, the count will not wrap around but will freeze once it reaches a value of 255. The table is generated by placing the VARDIG board in the data translation mode and passing a frame of data through the VARDIG board. This data is passed through a look-up table where data values representing a defective pixel are translated to a one bit in the low order position of the look-up table output. These one bits are counted for each group of two scan lines, resulting in 256 counts for 512 scan lines. The table can then be read by the 68000 for subsequent analysis to determine if the number and grouping of defective pixels warrants the rejection of the O-ring.

The VARDIG board receives data on the LBA and LBD bus and transfers data out on the LBC bus.

68000 Processor Board

The 68000 processor board is a standard off-the-shelf board available from Ominibyte, details of which are given in the Ominibyte Operator's Manual. The 68000 communicates with an external IBM XT or AT processor via a standard RS232 serial line.

Processing Sequence

Inspection is initiated at the camera board by a signal from an O-ring sensor which detects that an O-ring is about to enter the field of view of the camera. The camera board then automatically acquires the video data, digitizes it and as previously described, transfers a 512×512 image to one of the four frame buffers. The video acquisition of an image requires 200 ms. After an image is acquired the camera board issues an interrupt to the 68000. On a continuous basis the camera board transmits an interrupt to the 68000 every 1/60 of a second (16.67 ms); a period referred to as a frame period. At the fastest acquisition rate of one O-ring every 200 ms there will be 12 frame periods per O-ring.

The embodiment disclosed has been designed to operate in increments of one frame and all functions, other than the 200 ms image acquisition period and the final analysis of the defective pixel table, are designed to occur within one frame period. The operation of each board is under the control of the 68000.

The frame period consists of 525 scan periods which is further separated into two periods, a data period and a retrace period, with 512 scan periods in the data period and 13 in the retrace period. The scan period is also separated into a data period and a retrace period. There are 640 pixel times within a scan period; 512 being the data period and 128 being the retrace period.

All operations requested by the 68000 involve the transfer of a full frame of data from a frame buffer, through either the convolution or VARDIG board, and back to the original frame buffer, or another frame buffer, or in some cases two outputs to two frame buffers. The transfer of this data occurs during the data period of the frame time. There is then a dead period for the remainder of the frame of 13 scan periods. It is during this frame retrace period that the 68000 issues new commands to the various boards to set up the operation to be performed during the next frame time. An interrupt is sent to the 68000 from the camera board indicating the end of the frame's data period. The 68000 then has 412 microseconds to set up the next operation.

The system timing is designed such that at least one frame period exists between the completion of acquiring one image and the start of acquiring the next image. This always allows at least one frame period to empty the frame buffer being used to acquire an image so that it is free to acquire the next image.

The operations which occur during the 12 frame times and the activity of each board may be described as follows:

During frame one the camera board is inactive and the previous acquired image, contained in memory 1, is transferred to the convolution board where the gradient moduli and gradient angles are computed and transferred back to memories 2 and 3.

During frame number 2 the gradient angles ar transferred to the VARDIG board where the mean angles are computed and transferred back to memory 3. This step may be omitted in certain cases when smoothing the gradient angles through the mean angle process is not required.

During the third frame the newly created mean angles ar accessed, again by the VARDIG board, so that the angle count can be obtained and transferred back to memory 3. At the same time a parallel process is implemented which causes the original gradient modulus to be smoothed. This process transfers the gradient modulus from memory 2 to the convolution board where the gradient modulus is smoothed and transferred back to memory 2.

During the fourth frame the "weighted variability" is computed. This operation multiplies the smoothed gradient modulus by the angle count. The result is transferred back to memory 2.

During the fifth and sixth frame times the weighted variability is smoothed and clipped. This operation reduces noise in the weighted variability results by spreading out and clipping small defect areas. The smaller the area the more likely it is to disappear during this process. The final operation occurs during frame seven which takes the smoothed and clipped weighted variability and transfers it from memory 2 to the VARDIG board where the defective pixel table is generated.

During frames 2 through 12 the camera board is free to acquire the next image by inputting camera data and outputting the digitized image on the video bus to memory 1. Note that memory 4 is not used during this process, but was provided with the prototype system to aid in system check-out. The acquisition of the next image, of course, does not have to start at frame 2.

In the description to follow, references will be made to pixels, pixel arrays, pixel locations, etc., whether referring to the original image contained in memory 1 or various forms of the "processed image" in memories 2 and 3. In essence, each of memories 2 and 3 contain a memory array directly mappable on a one-to-one basis to the array of memory 1 in which the original image is stored, so that there is a one-to-one correspondence between pixels, pixel locations and pixel arrays between the memories whether of the original image in memory 1 or in the processed images of memories 2 and 3.

While input and output bus selection occurs automatically on the convolution and VARDIG boards based on the modes they have been set to, this is not the case for the memory boards. Memory board bus selection must be specified by the 68000 for each memory operation. In addition, pan and scroll selections must be made for each memory to compensate for pixel delays and line offsets which occur when the convolution or VARDIG boards are used. In addition to mode selection a look-up table selection must be specified any time the convolution or VARDIG boards are used. Generally a different look-up must be selected for each operation. These details are subsequently described in conjunction with the descriptions of the individual board block diagrams.

The 68000 multiplexes its operation between the control of the various boards and the analysis of the previous O-ring's defective pixel table. The results of this analysis will indicate O-ring acceptance or rejection. If the O-ring is rejected a signal is transferred from the 68000 to a mechanical reject mechanism.

Detailed Board Description

Camera Board

Figure 3:
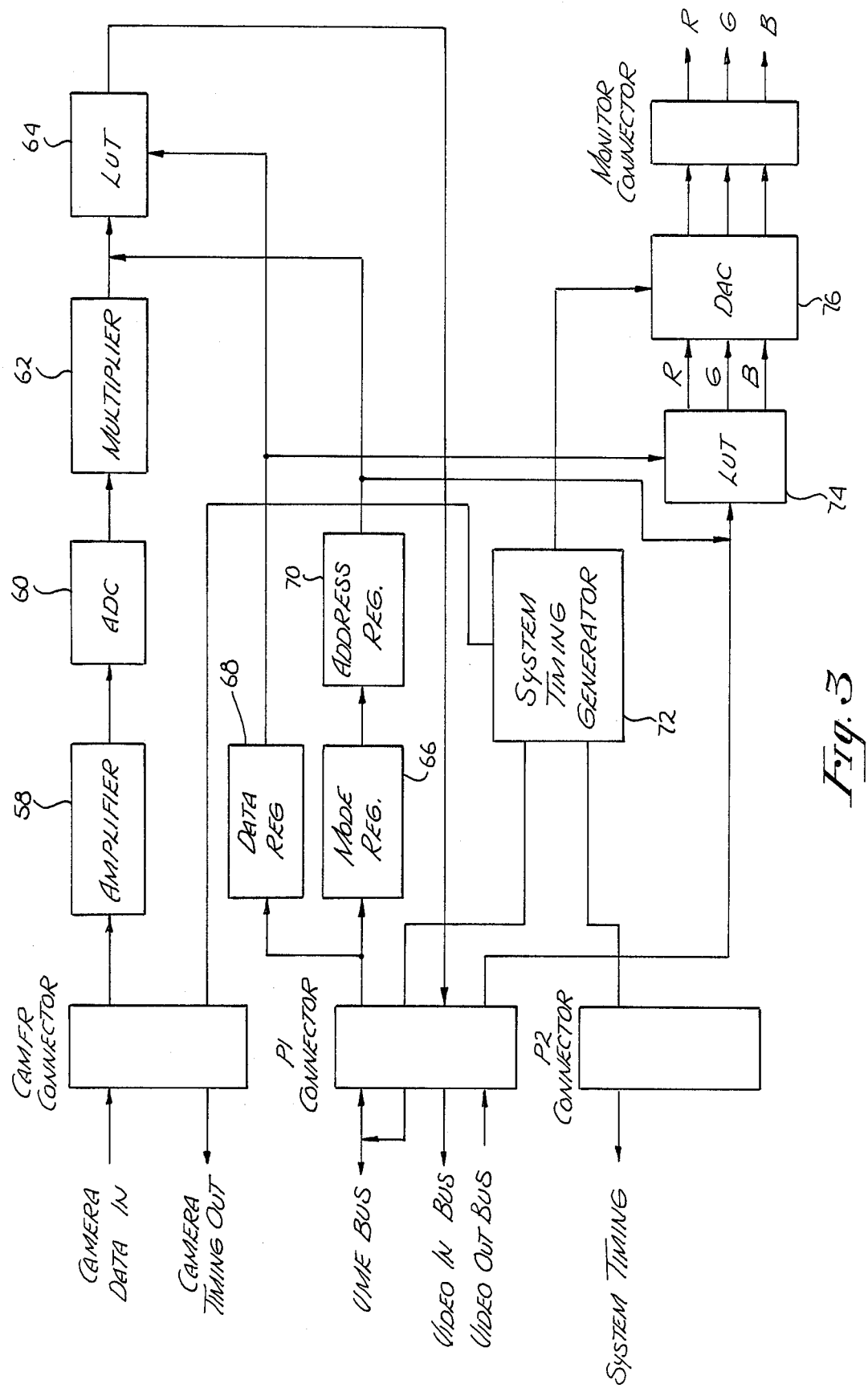
FIG. 3 is a block diagram of the camera board 40 of the system of FIG. 1.

FIG. 3 is a block diagram of the camera board. The camera board consists of four major sections; camera interface, VME bus interface, system timing, and monitor interface.

The camera interface accepts camera data input and processes this data through four separate sub-sections. The amplifier section 58 provides level shifting and signal amplification to match the camera input data to the input requirements of the analog to digital converter (ADC) 60. The ADC is a flash converter which can operate up to 20 MHz conversion rate and provide as its output an 8 bit digital value which is transferred to the multiplier 62. The multiplier provides scaling of the 8 bit input value with a separate scale factor provided for each pixel in the 512 pixel scan line. The look-up table (LUT) 64 consists of four 256×8 look-up tables. These look-up tables can be loaded by the 68000 via the VME bus. The look-up table to be used during the data acquisition cycle is selected by the mode register 66.

The VME bus interface consists of an 8 bit data register 68 and an 8 bit mode register 66. The 8 bit data register provides temporary storage of a byte of data to be loaded into either the camera look-up table or the monitor look-up table. The address register 70 provides an 8 bit address byte to either the camera or the monitor look-up table The mode register 66 controls the selection and loading of the look-up tables 64 and provides the mechanism to clear and increment the address register 70. The mode register also holds the interrupt acknowledge bit which is transferred to the camera board from the 68000 indicating that a camera board interrupt has been received Controls common to VME bus operation are not shown in this section.

The system timing generator 72 provides the timing signals required for camera operation, the timing required to drive the frame and end of camera cycle interrupts to the VME bus, system timing to the frame buffer and other boards consisting of camera timing used to synchronize the transfer of camera data to the frame buffers and frame and scan timing used to operate the memories at the 60 Hz data processing rate or the 30 Hz monitor 56 display rate. The system timing section also generates the timing required to provide horizontal and vertical sync to the display monitor.

The output of the camera look-up table drives the video out bus which transfers camera data to the frame buffers.

The monitor control section consists of three look-up tables 74, one each for red, green, and blue outputs. These look-up tables are driven by byte serial data from the video in bus. Each look-up table provides a separate 8 bit output to a high monitor drive outputs for red, green and blue and provides video sync on the green channel.

Frame Buffer

Figure 4:
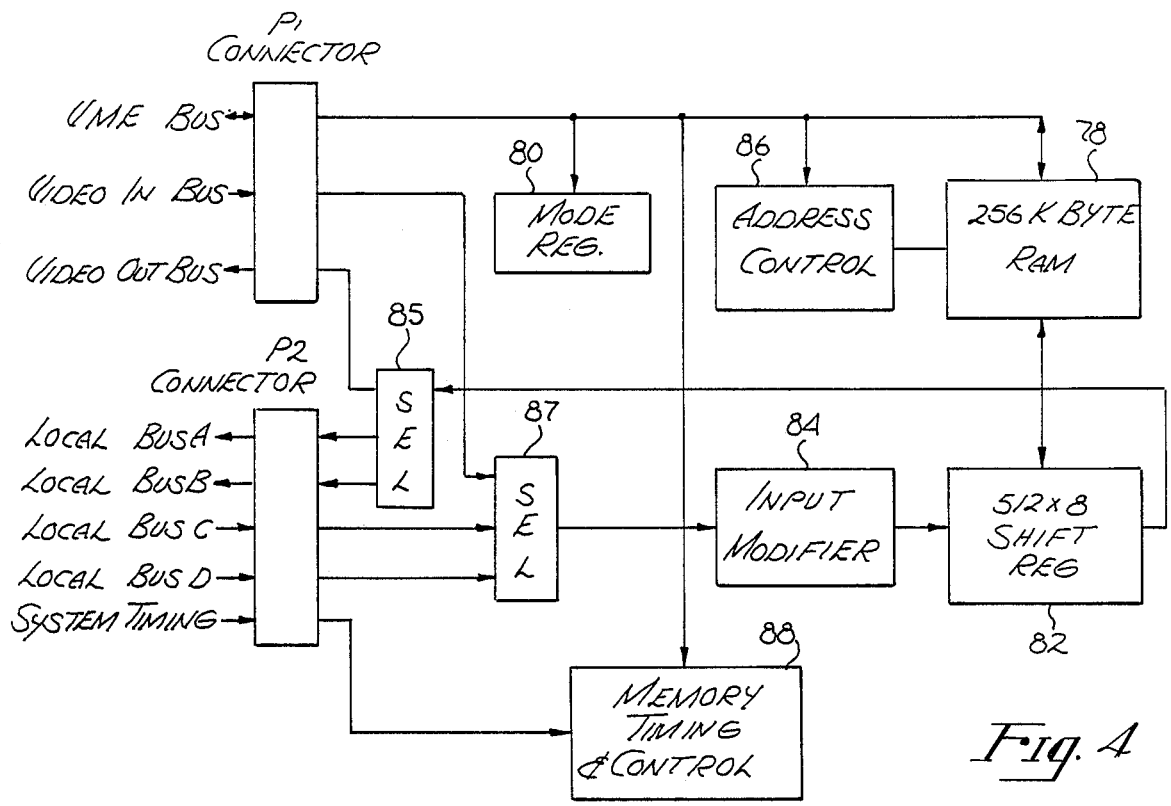
FIG. 4 is a block diagram of each of the frame buffer boards 42 through 45 of the system of FIG. 1.

FIG. 4 is a block diagram of each frame buffer. The frame buffer has four major sections; VME bus interface, frame memory, local bus interface, and memory timing and control. The VME bus interface allows transferring a byte between the 68000 and the frame memory 78 (256K byte RAM). The VME bus also allows the 68000 to write either of two byte wide mode registers 80.

The frame memory is constructed with 32 64K bit video RAMS and stores one byte of data for each pixel in a 512×512 pixel array. The 512×8 bit shift register 82 is an integral part of the video RAM IC's and provides a convenient mechanism for transferring serial byte wide data to the local bus and the video in bus. This shift register also accepts serial byte wide data from the local bus and video out bus. The input modifier 84 allows accepting the input data unmodified, inverted, set to a constant of all zeros, or set to a constant of all ones. The address control section 86 of the frame memory 78 allows the memory to be addressed from the VME bus or to be automatically sequenced for video or local bus operations. The address control allows image data from the 68000 to be automatically sequenced horizontally along a row or vertically along a column.

The video bus and local bus interface allows the transfer of memory data between the frame memory and the camera board (video in bus, video out bus) or to the convolution and VARDIG boards (local bus A, B, C, D) at a 20 MHZ rate. Mode register decoding allows only one output and one input to be selected at a time The memory timing and control section 88 receives timing signals from the camera board via the system timing signals and timing signals associated with VME bus transfers. This section controls the timing of the memory cycles and the serial input/output shift rate The memory timing can be selected for 5 Hz camera input rate, 30 Hz monitor display rates, or 60 Hz data processing rate. In addition the memory timing and control section provides control of scroll and pan which corrects for pixel delays and vertical off-sets caused by external processing.

Four memory frame rate selections are available. The 60 Hz non-interlaced frame rate is used when processing a frame of data through the convolution or VARDIG boards. The 5 Hz frame rate is used when inputting an image from the camera board. Either a full screen image (512×512) or a quarter screen image (256×256) can be loaded into the frame buffer. When loading a 256×256 image only even pixels and even lines from the 512×512 camera image are loaded. A 30 Hz interlaced frame rate can be selected. This is used when transferring the image from a frame buffer to the display monitor.

The output bus select registers allows the serial byte wide data from the frame buffer to be transmitted to the camera board (via the video out bus) or to local buses A and B via selector 85. The video in bus is normally selected via selector 87 when transferring information to the monitor via the camera board. In this case the 30 Hz interlaced frame rate is chosen. However, the video in bus can also be used to transfer information out of the memory at the 5 Hz frame rate in order to simulate camera data for transfer to other boards (not disclosed herein) for other purposes. Local buses A and B are used when processing a frame through the convolution or VARDIG board. When local buses A and B are selected through selector 85, the memory frame rate is set to 60 Hz.

The mode register 80 A bits used for input bus select via selector 87 allow inputting data from the camera (video in bus) or from the convolution and VARDIG boards (local buses C and D). When inputting on the video in bus the 5 Hz frame rates are selected When inputting on local buses C or D the 60 Hz frame rate is selected.

The memory input modifier control bits in mode register A provide a convenient way of inverting the input data or setting the full frame buffer to all zeros or all ones. Input data inversion can be used when inputting data either from the camera or convolution or VARDIG boards Setting the memory to all zeros or all ones is usually used with the 60 Hz frame rate. This allows setting or resetting the full frame in 1/60 th of a second. For this mode input and output buses do not need to be selected.

Mode register 80B bits provide selection of the horizontal offset, vertical or horizontal sequencing of 68000 data transfers, selection of the upper half or lower half of the screen for loading a 256×256 image, and vertical off-set.

Horizontal off-set is used to compensate for delays incurred when transferring frame data through the convolution or VARDIG boards. This delay would normally cause the returned image to be off-set to the right. The amount of off-set depends upon the type or process being performed.

When transferring a block of data between the 68000 and a frame buffer the data is normally sequenced from the left to the right starting at the top line of the displayed image. Mode register 80B bits allows the selection of vertical sequencing which orders data from the top to the bottom starting with the left most column.

When loading a 256×256 image, mode register B selects the upper or lower half of the screen. When a 256×256 image is loaded it is always loaded into the right half of the screen. When a second 256×256 image is loaded it will again reside in the right half and the image originally in the right half will automatically be shifted to the left half.

Mode register B also provides vertical off-set to compensate for convolution and VARDIG board processing. For instance, when processing includes a 3×3 pixel matrix operation the results should be returned one line up. Other off-set values must be selected when performing the angle count operation using a 2×2 or 3×3 cell.

The Convolution Board

Figure 5:
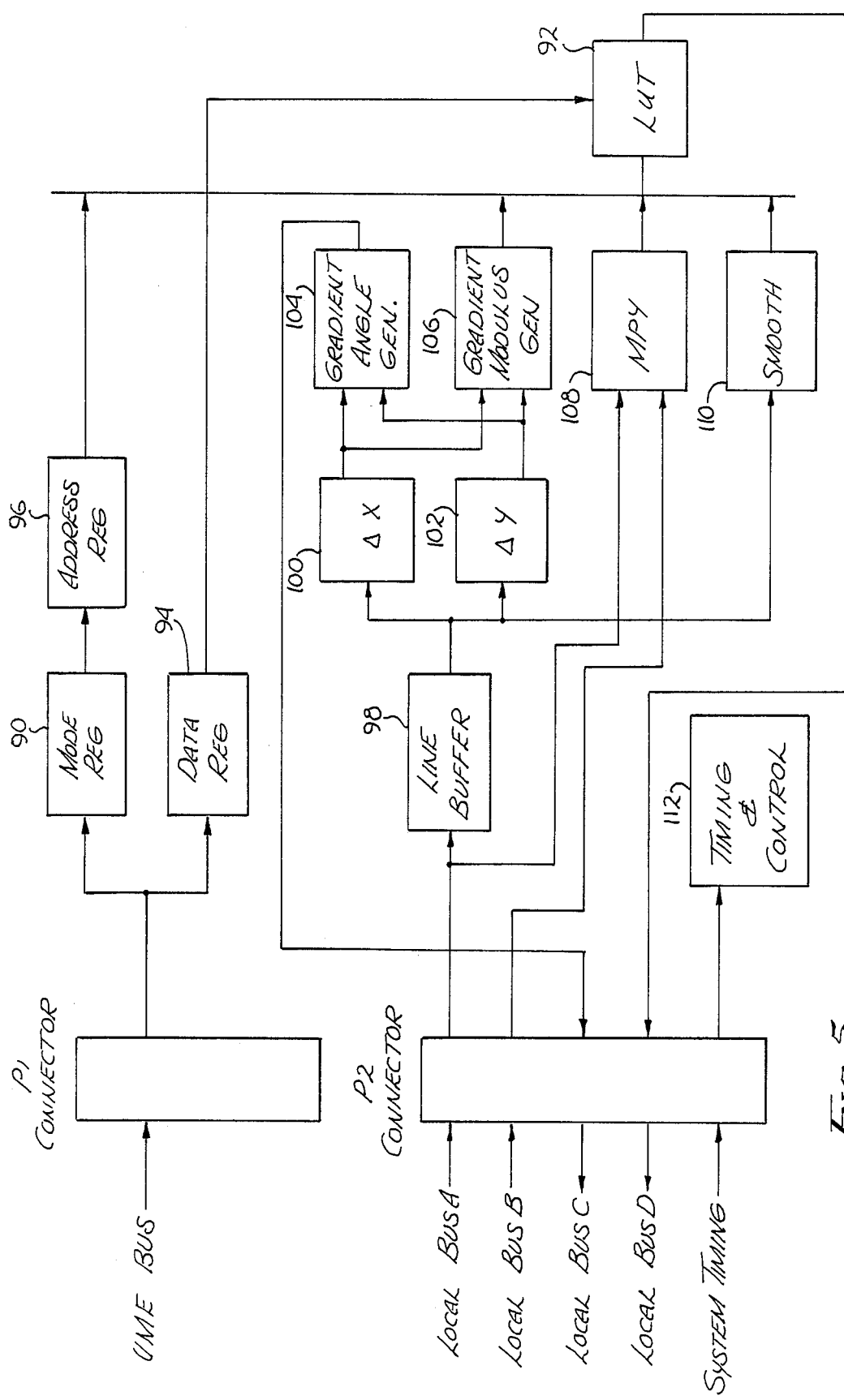
FIG. 5 is a block diagram of the convolution board 46 of the system of FIG. 1

FIG. 5 provides the block diagram for the convolution board. The convolution board has four major sections; VME bus interface, line buffer, image processing, and timing and control.

The VME bus interface allows the 68000 to select the mode of operation and load the look-up table. The mode register 90, 8 bits wide, selects the operation to be performed and controls the process of loading the look-up tables 92. The mode register also selects which of 8 separate 256×8 bit look-up tables will be used during the time an image is processed. The data register 94 holds the data to be loaded into the look-up table and the address register 96 provides the write location The line buffer 98 stores three complete scan lines. This is required in order to process a 3×3 pixel array.

The image processing section provides both arithmetic and trigonometric operations. Two arithmetic section 100 and 102 provide a delta X and delta Y value. These values are used to generate the gradient angle and the gradient modulus. Both the gradient angle and gradient modulus are generated at the same time using two other arithmetic sections 104 and 106. The multiply unit 108 will multiply an 8 bit value inputted on local bus A by a 3 bit value inputted on local bus B. The smoothing module 110 will find the average of a 3×3 pixel array and return this average to the center pixel location. All outputs except for the gradient angle are passed through the look-up table 92 before they are transferred out on local bus D. The gradient angles are transferred out on local bus C.

The timing and control section 112 synchronizes the image processing with the data flow from the frame buffers and controls the sequencing of the line buffer.

The VARDIG Board

Figure 6:
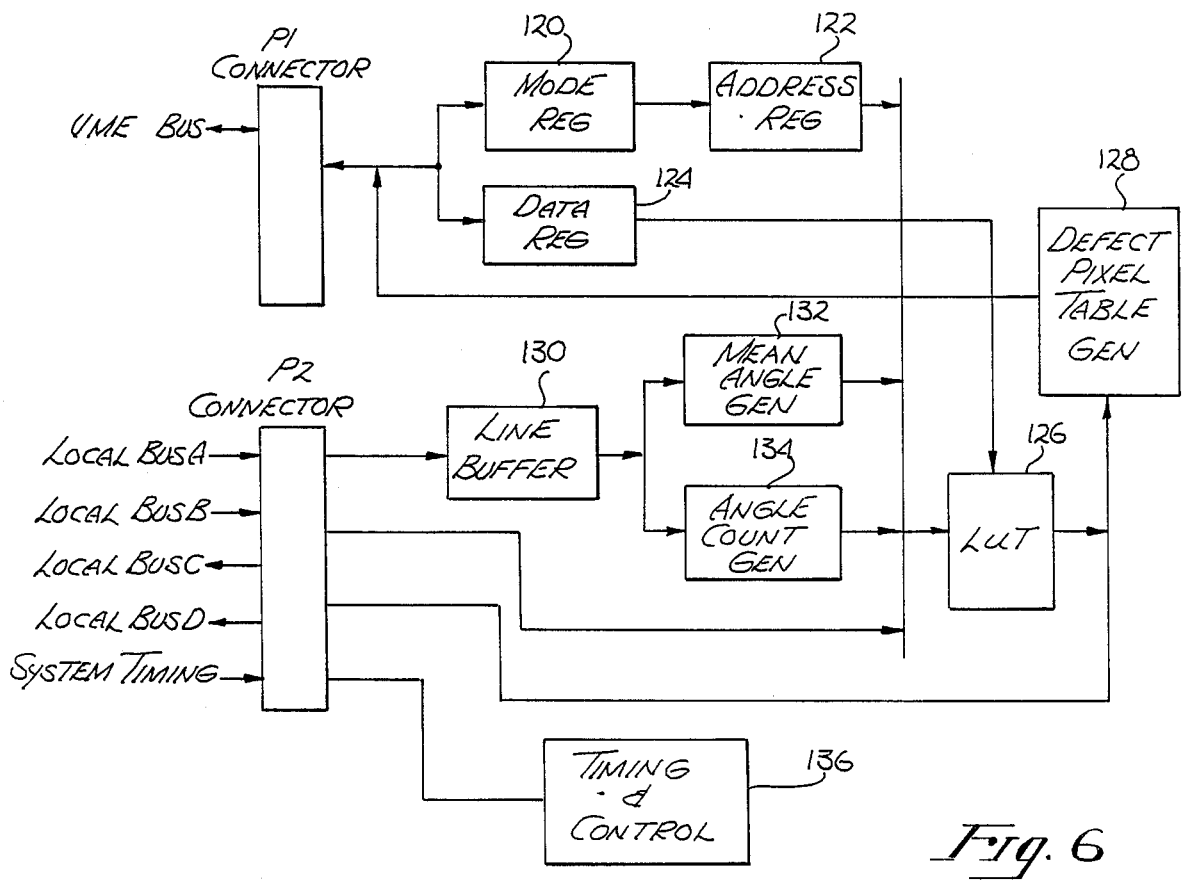
FIG. 6 is a block diagram of the VARDIG board 48 of the system of FIG. 1.

FIG. 6 provides the block diagram for the VARDIG board. The VARDIG board has five main sections; VME bus interface, defect pixel table generator, line buffer, image processing, and timing and control.

The VME bus interface provides a means of setting the mode register 120, which controls and selects the processing options, and the setting of the address and data registers 122 and 124 for the purpose of loading the output look-up tables 126. In addition the VME bus is used to read the defect pixel table 128 so that it can be processed in the 68000.

The defect pixel table provides a defective pixel count which can be used to analyze the nature of surface defects. A byte is read from the defect pixel table by a read operation using the data registers port address The defect pixel table has 256 locations. These locations are addressed by the address register.

The line buffer 130 is similar to that used in the convolution board. It stores four scan lines and provides three lines out in parallel for processing by the mean angle generator 132 and the angle count generator 134.

Three image processing operations can be selected; mean angle, angle count and translation. Separate generators are provided for the mean angle and the angle count. No processing is performed during the translation mode prior to the look-up table. The translation mode is used in two cases: to translate image data via the look-up table operation, and to activate the defect pixel table operation.

The timing and control section 136 provides synchronization of the image processing operation with the data flow from the frame buffer memories It also controls the sequencing of the line buffer

Having now described the hardware organization of the preferred embodiment of the invention, and in conjunction therewith the operation of the various elements of the system, a general more integrated overview of the operation of the system may now be presented. Once a frame of image data has been gathered, the first step in the processing is to generate the Delta X and Delta Y information utilizing a sliding window as illustrated in FIG. 7a. This figure illustrates the use of a 3×3 pixel array, that is an array 3 pixels wide by 3 pixels high, though arrays of other sizes such as, by way of example, 5×5 or 7×7 may be used. In any event, assuming a 3×3 pixel array is used, the Delta X and Delta Y values are determined as illustrated in FIG. 7b. As may be seen in FIG. 7b, the Delta X value is equal to the difference between the right hand three pixel values in the cell and the left hand three pixel values, with the Delta Y being the difference between the sum of the top three values and the sum of the bottom three values. Both the Delta X and the Delta Y of course are signed numbers.

The second step in the processing of the information is to generate the gradient modulus and the gradient angle for each pixel in the array. The gradient modulus of course technically is the square root of the sum of the squares of Delta X and Delta Y. In the preferred embodiment this is approximated as the sum of the absolute values of Delta X and Delta Y, which is done in the gradient modulus generator of FIG. 5. The gradient angle in the preferred embodiment is a 3 bit number and accordingly, is rounded off to 45 degree increments as illustrated in FIG. 7c. Here again, for each combination of Delta X and Delta Y, there is a specific gradient angle, the gradient angle being generated by the gradient angle generator also shown in FIG. 5. The gradient modulus and gradient angle are immediately generated as each combination of Delta X and Delta Y becomes available so that the Delta X and the Delta Y values themselves are in general not stored.

The next step in the processing is to generate from the gradient angle information the mean angle for each cell. This actually is an optional step in that the mean angle may or may not be required for further processing, depending upon the specific method used, as shall be hereinafter explained. Assuming for the moment that the mean angle is required, the mean angle for all the pixels in the cell (a 3×3 cell and a 2×2 cell being illustrated in FIG. 7d) is determined by the mean angle generator 132 of FIG. 6 and stored in a predetermined pixel location in the cell, the center location in a 3×3 cell or the upper left corner of a 2×2 cell as illustrated in FIG. 7d.

The next step in processing the information is to determine the variability in the gradient angles. Here any of a large number of techniques, or for that matter more than one technique, may be used depending upon the application. In the case of the inspection of O-rings wherein the ideal surface is toroidal, two methods which may be used to measure the variability are first, the deviation from the mean, and second, the angle count. The deviation from the mean is equal to the square root of the sum of the squares of the difference between each particular gradient angle and the mean angle for the 3×3 array of cells. While this or an approximation thereof could be implemented, in the preferred embodiment the angle count is used instead. The angle count is merely a count of the number of unique gradient angles or unique mean angles within a 3×3 cell array. Also, as stated before, the cell size to be selected for the variability can be chosen differently. In particular, there are three array configurations which can be used for the angle count, each consisting of a 3×3 array of cells. According to the convention used, the cell sizes of 1×1, 2×2 or 3×3 pixels may be used, the 2×2 cell having the gradient angle or mean angle value stored in the upper left element of the cell and the 3×3 cell having the gradient angle value or mean angle located in the center element. When a multiple element cell is used the resulting angle count is stored in all elements of the center cell, with the next array being analyzed displaced one cell therefrom. These of course were illustrated in FIG. 2.

The next step in the processing is to smooth and/or clip the gradient modulus as desired, and to smooth and/or clip the variability, also as desired. These operations of course are accomplished by a smoothing operation performed by the convolution board and by look up tables. In that regard, the characteristics and capabilities of look up tables, particularly look up tables which may be loaded under software control, should be particularly noted. The look up tables in general are memories which have as their input address a data value (or in some cases, more than one data value, each data value making up part of the complete address) with the output being the value stored at the addressed memory location. The output value may be the same as the input, may be all zeros, may be all 1's, or have any relation to the input one desires. In that regard, clipping as used herein is generally used to mean either truncating values for returning a fixed output for all inputs equal to or greater than a particular value, or thresholding wherein a zero output is returned for all values equal to or below a minimum value, or both. Smoothing on the other hand generally relates to the averaging of a neighborhood of data points, usually to remove the effect of local data anomalies. In the present invention clipping in the form of thresholding tends to eliminate or at least grossly reduce the effect of low values which in themselves do not indicate any condition of concern but which, if not eliminated or at least minimized, will have a cumulative effect across the entire image and thereby may result in a false indication of a reject condition. Clipping in the form of truncating data, on the other hand, generally has the effect of providing a limit on how much weight a bad point or area will have, thereby requiring a certain minimum number of bad points before a reject indication is provided. In general, since the mapping between the input to the look-up table and the output thereof can be fully tailored as desired to achieve clipping (truncating or thresholding), scaling, shaping, masking, etc., the process is referred to herein in a most general sense as mapping or transforming of the data in a predetermined manner.

The next step in the processing is to combine the gradient modulus of each cell with the variability of the cell, in the preferred embodiment disclosed for the inspection of O-rings, such combining being by way of multiplication. The results one obtains from this operation illustrate one of the major advantages of the present invention. In particular, the gradient modulus around the edges of an article such as an O-ring, being dependent upon the rate of change of light intensity, will be very high as normally, regardless of the item being inspected, there will be a relatively sharp contrast between the article being inspected and the background. On the other hand, for articles like O-rings where the edges do not have sharp corners the gradient angle measurement at the edges will be quite regular, so that the variability of the gradient angle will be quite low, if not zero. Thus by thresholding the variability as hereinbefore described, the variability characteristic of edges is made equal to zero, so that when the variability and gradient modulus are multiplied, the product itself will be zero. On the other hand, though the gradient angles would be expected to uniformly vary over the area of the O-ring image for a good O-ring and thus the variability over the area of the image of a good O-ring will also be low, surface defects such as caused by lack of mold filling, etc., will cause fairly localized gradient angle changes and thus a variability well above the threshold. Such defect will also give a relatively localized difference in light intensity so that the gradient modulus at such locations will also be well above any threshold, thereby resulting in a modulus-variability product indicative of the adverse local condition. (Areas of substantially uniform intensity may also exhibit a high variability because of a random drift in the gradient angle, but the gradient modulus of such areas will be zero or at least very low.) Thus it may be seen that the combination of the gradient modulus and variability eliminates what would otherwise be the predominant effect of the edges of the article being inspected, while at the same time preserving substantially all indicia of surface defects on the surfaces of the article being inspected. It will also be noted that the variability as well as the gradient modulus provide relatively good indications of surface defects on the article being inspected, so that either variability alone or preferably the variability combined with the gradient modulus will provide a useful inspection parameter. Also, since both the variability and gradient modulus respond to defects on the surface of the article being inspected, the product of the gradient modulus and variability in essence enhances the defect detection as the combination is equivalent to combining data containing defect information from two different forms of the original image to provide a combined or statistically enhanced evaluation.

There are of course other ways to combine the variability and gradient modulus other than by simply multiplying. By way of specific example, since the variability is very low at the edges of the article, the variability could be used to create a binary mask for the gradient modulus so that the gradient modulus itself would be used for defect detection without interference from the edges of the article. It is believed best however, in most applications to combine the gradient modulus and variability both because of the edge detection suppression characteristics of the variability and the somewhat independent defect detection capability of both the gradient modulus and variability. On the other hand, as shall be subsequently described, the variability may in some instances be used to enhance the effect of the edge of the article being inspected in a manner other than a simple inverse binary mask generated by the variability.

The last step prior to the assembly of the defective pixel table is to smooth and again clip the resulting data one or more successive times. The net effect of this is the removing of small groupings of resulting defective image elements without significantly effecting larger groupings thereof. By way of specific example, for a single isolated defective image element, smoothing by averaging the element with its eight immediate neighbors will cut the defective image element value by a factor of nine, though of course the effect of that image element will spread to the eight neighboring elements. Clipping (thresholding) of this smoothed value will further reduce the amplitude of the defective image element and the neighboring elements, so that a repetition of the smoothing and clipping will cause the effect of the isolated defective image element to disappear. Groupings of defective image elements of substantial size however, will not similarly be removed, as the net effect of repeated smoothing and clipping will be to smear the edges of the group, but unless excessively repeated, not to effect the center of the group. Obviously here again the extent to which one wants to smooth and clip (and when) will be dependent upon the particular application and the results desired thereby. Of course once the desired smoothing has been achieved, the defective image elements may simply be counted and compared against a predetermined accept reject level for final disposition of the article being inspected.

It should be noted that while the variability of the gradient angle is highly useful to eliminate the effect of edges as hereinbefore described, use of the variability in conjunction with the gradient modulus or intensity gradient is also highly useful to detect certain edges in some instances. By way of example, in the preparation of string beans for canning, it is of course desired to have the stems removed from all beans for obvious reasons. Accordingly, it would be desirable to be able to inspect the beans for the presence of stems by an automatic inspection device prior to the canning operation. This can be done when utilizing the present invention as follows:

First the geometry of the system is chosen so that a typical stem in the image will have a width appearing as a fine line, on the order of two or three pixels Consequently, while the variation in gradient angle along either edge of the image of the stem will be quite low because the stem will be relatively free of sharp bends, the gradient angles for one side of the stem image will be 180 degrees opposite the gradient angles for the other side. Consequently, the stems are characterized by gradient angles which are close together and opposite To detect this condition, one might calculate the variability as the deviation from the mean or alternatively, by the use of some other algorithm to produce a measure of variability. Regardless of what measure is used however, in general only the stems will show up in this manner, as the body of a string bean will of course provide opposite gradient angles for the opposite sides of the image thereof, but these gradient angles will not be close together.

Assuming for the moment that one intends only to inspect for stems at that particular stage of processing of the string beans, it should be noted that shadowed regions or surface imperfections may cause the gradient angles to be close together and opposite in various regions of the image within the body of the bean. Combining the gradient angles with the gradient modulus can effectively eliminate the false sensing of these regions however, so as to leave only the sensing of the stems. In particular, as stated before, the intensity gradient modulus at an edge, whether it be an edge of a stem of a string bean, O-ring or other object being inspected, is very high, whereas in general for an object like a string bean, the gradient moduli over the area of the image of the string bean is much lower for substantially all shadows and imperfections. Accordingly, if the gradient angles and gradient modulus are combined, such as by way of example, by multiplying as hereinbefore described with respect to O-ring inspection, the large gradient modulus at the edges of the image, both for the bean body and the stem, will result in the product maintaining the gradient angle information for the edges, though the low gradient modulus across the bean body image will result in a low product of the angle variability and the gradient modulus, which after smoothing and/or thresholding before, after or both before and after combining the variability and modulus gradient, will remove any effect of high angle variability within the image of the body of the string bean.

It should be noted that the foregoing allows the detection of the presence of a stem on a string bean of varying size and shape without any particular alignment of the string bean, yet at a very high inspection rate. Actually, to have the stem represent a fine line in the image, the individual string bean generally only occupies a small part of the image area, so that there may be many string beans in the field of view. This in turn raises the possibility of two string beans being close together so that one can get two closely spaced edge transitions in the image, the first being the transition from the first bean body to the space between the two string beans, and the second of course being the transition onto the image of the body of the second string bean. Note however, that the transitions are string bean to background to string bean, rather than background to stem to background. While the gradient modulus is substantially insensitive to the difference between a light to dark transition and a dark to light transition, the gradient angles will be reversed for these two cases, so that the gradient angles in relation to the adjacent opposite gradient angles will indicate this condition, and upon appropriate processing can be used as a mask to eliminate any false indications of too closely spaced string beans.

It can be seen from the foregoing that use of the gradient angles representing the local direction of the light intensity gradient provides a great deal of information not readily apparent from the modulus of the light intensity gradient alone. In some applications, the gradient angles themselves could represent useful information, such as by way of example, indicating the orientation of long parts by sensing the orientation of the sides thereof or reflection from the body thereof, particularly when the unwanted information is masked away by a mask derived from the gradient modulus information. In general, because the gradient angles are scalar quantities, the data can effectively be normalized to a fixed alignment by merely providing an offset angle to the data, i.e., a one dimensional correction rather than having to do a full two dimensional matrix rotation as is required in some prior art systems. In most applications however, the primary information is contained in the manner in which the gradient angle varies in a local region, herein referred to as the variability, which variation may be quantitatively measured in different ways. As has been illustrated, when detecting such things as stems on string beans, matching the physical parameters to the processing parameters (pixel size, cell size, method of determining variability, etc.) allows the system to detect a stem on a string bean even when many string beans are within the field of view, and to do so at an extremely high speed. It is this capability which gives the system of the present invention greater inspection versatility and capabilities than prior art systems, and which allows the use of the present invention system for the inspection of great volumes of a product having a very low per unit value.

In the preceding descriptions, various examples of methods for determining the variability in the gradient angles have been presented. These in general have included the deviation from the mean gradient angle and angle count. Another example of variability which might be used is the range of angle difference within a neighborhood (the maximum being 180 degrees). In a more general sense, the variability in the gradient angles within a neighborhood is simply a measure of the fluctuation of the gradient angles from a uniform direction. In a still more general sense, the variability can be in effect any predetermined dependence on the pattern of gradient angles within a neighborhood. By way of specific example, using the 3×3 array for the neighborhood and a 3 bit number (8 discreet angles of 45 degree increments) for the gradient angles, there are $8^9$ possible patterns of angles for which variability is to be determined. While one could work with that number of unique measures of variability, in general symmetries and other redundancies will grossly reduce the number of distinct quantative measures of variability. By way of specific example, the angle count hereinbefore mentioned for the exemplary system has only 8 distinct possibilities, as the gradient angle count must be an integer not less than one nor greater than 8. Thus in this case, the $8^9$ possibilities in theory reduce to 8 possibilities in practice. Similarly, the range of angle difference, if used, reduces the $8^9$ possibilities in theory to 5 possibilities in practice, as the range of gradient angle differences within the neighborhood is an integer of not less than 0 or more than 4. The point being made of course is that one will normally determine variability by testing various mathematical approaches and picking the approach which provides the best imperical results, though this is by no means a limitation to the present invention, as one could readily decide to determine variability in a particular application by analyzing typical images to find patterns which readily characterize the characteristic being inspected for and characterizing such patterns as patterns of high (or low) variability without having any special compact mathematical expression (angle count, deviation from the mean, range of angle, differences, etc.) for doing so. The important point of course is to determine the gradient angles and to convert the gradient angles in each neighborhood to a measure of variability which alone, together with the modulus or with some other parameter, is used to characterize the object being inspected as acceptable, unacceptable, as being of a particular grade or quality, etc. in regard to some predetermined characteristics or parameters, whether by multiplying, through the use of a look up table, by a masking operation or otherwise, or combinations of the foregoing.

Also, in the description of the preferred embodiment, the gradient modulus was defined as technically being the square root of the sum of the squares of Delta X and Delta Y, which in the preferred embodiment is approximated as the sum of the absolute values of Delta X and Delta Y. It is to be noted however, that other measures of the modulus may readily be used depending upon the particular application and/or desired result. By way of example, one might use the sum of the absolute values of Delta X and Delta Y raised to any other power, or alternatively, one might select the larger of the absolute value of Delta X and the absolute value of Delta Y. Still further measures of modulus would include, for each 3×3 pixel array, the largest Delta for each of the 8 compass directions of the array, which reduces to the largest absolute value of the Delta for the 8 unique directions of the array.

One of the aspects of the present invention which substantially enhances its utility and provides flexibility and ease of tailoring to a particular application is its physical organization. In particular, it has already been pointed out that the look up tables may be loaded under software control, and may be used to change the data in ways ranging from no change at all to clipping (truncating and thresholding), shaping the data, creating a mask from the data or any combinations of the foregoing. The use of a multiple bus system allows the transfer of the data back and forth between the frame buffers, convolution board and VARDIG board during processing so that the various operations may be accomplished in a manner and sequence based upon the selection of modes for the various boards and control of the buses. The multiple bus structure of course allows transfers to occur simultaneously, resulting in a high degree of parallel processing in the system. This, coupled with the fact that each subsystem will operate with substantially any camera running at normal speed and keep up therewith, provides great flexibility in the application of the system. In that regard, a two-dimensional camera will in general speed the image data acquisition process with a color camera perhaps providing additional data useful for the inspection process. Finally, the connection of all subsystems to a bus structure controlled by a processor which itself has standard communication capabilities with microcomputers and the like provides simple, low cost and highly flexible overall initialization and control of the system and utilization of the inspection information Thus while the present invention has been disclosed and described with respect to certain preferred embodiments thereof, and exemplary uses of the invention have been provided, it will be understood by those skilled in the art that various changes in form and detail may be made therein without departing from the spirit and scope thereof.

We claim:

1. A method of inspection of an article comprising the steps of
   (a) digitizing the image of an article to be inspected to provide a first image array of first data values, each first data value being a digital representation of the intensity of the respective pixel of the image
   (b) transforming the first image array to a second image array of second data values, each second data value indicating the direction of the intensity gradient for each respective first data value
   (c) for each second data value of the second image array, determining a single third data value, each third data value being related to a respective second data value and responsive to the variability of the second data values within the neighborhood of that respective second data value, each neighborhood of each second data value being no more than a 3×3 neighborhood and being chosen so that each second data value has the same relative neighborhood location as each other respective second data value has to its neighborhood location, whereby the second image array is transformed into a third image array, and
   (d) characterizing the article being inspected utilizing, at least in part, the third data values.

2. The method of claim 1 further comprising the step of calculating, for each second data value based on its respective neighborhood of second data values, a mean second data value, and wherein, in step C, each third data value is responsive to the variability of the mean second data values within each corresponding neighborhood of mean second data values.

3. The method of claim 2 wherein each mean second data value is calculated for a corresponding neighborhood of second data values comprising an N by N array of second data values.

4. The method of claim 3 wherein N is two or more.

5. The method of claim 1 wherein in step C, each third data value is responsive to the number of different values of the second data values within the corresponding neighborhood of second data values.

6. The method of claim 1 further comprising the step of calculating, for each corresponding neighborhood of second data values, a mean second data value, and wherein, in step C, each third data value is responsive to the number of different values of the mean second data values within the corresponding neighborhood of mean second data values.

7. The method of claim 6 wherein each mean second data value is calculated for a corresponding neighborhood of second data values comprising an N by N array of second data values.

8. The method of claim 7 wherein N is two or more.

9. The method of claim 1 further comprised of the steps of
   (e) calculating an array of fourth data values, each fourth data value being responsive to the magnitude of the intensity gradient at the respective image portion as indicated by the array of first data values
   (f) combining each fourth data value with a respective third data value prior to step (d) of claim 1, whereby the article being inspected is characterized by the combination of the third and fourth data values.

10. The method of claim 9 wherein said array of fourth data values are smoothed prior to step (f).

11. The method of claim 9 wherein said fourth data values are transformed prior to step (f).

12. The method of claim 1 wherein each second data value is calculated from a corresponding N by N two dimensional array of first data values.

13. The method of claim 12 wherein N is at least 2.

14. The method of claim 12 wherein N is 3.

15. The method of claim 1 wherein said array of first data values are smoothed prior to step (b).

16. The method of claim 1 wherein said second data values are transformed prior to step (c).

17. The method of claim 1 wherein said second data values are transformed prior to step (c).

18. The method of claim 1 wherein said array of third data values are smoothed prior to step (d).

19. The method of claim 1 wherein said third data values are transformed prior to step (d).

20. The method of claim 1 wherein step C, each third data value is responsive to the number of distinct second data value pairs within the corresponding neighborhood of second data values which represent predetermined substantially opposing directions of intensity gradients.

21. A method of inspection of an article by analyzing the image thereof comprising the steps of
   (a) digitizing on a line by line basis at least part of the image of an article to be inspected to provide a first image array of first data values, each first data value being a digital representation of the intensity of the respective element of the image
   (b) transforming the first image array to a second image array of second data values, each second data value indicating the direction of the intensity gradient for each respective first data value
   (c) for each second data value of the second image array, determining a single third data value, each third data value being related in relative array position to a respective second data value and responsive to the variability of the second data values within the neighborhood of that respective second data value, each neighborhood of each second data value being no larger than a 3×3 neighborhood and chosen so that each second data value has the same relative neighborhood location as each respective second data value has its neighborhood location, whereby the second image array is transformed into a third image array, and
   (d) characterizing the article being inspected utilizing, at least in part, the third data values.

22. The method of claim 21 wherein, in step (c), each third data value is responsive to the variability of the second data values within a 3×3 neighborhood of that respective second data value.

23. The method of claim 22 wherein the 3×3 neighborhood is a 3×3 pixel neighborhood.

24. The method of claim 22 wherein the 3×3 neighborhood is a 3×3 neighborhood of cells, each cell being an N×N array of pixels having a representative second data value for each cell.

25. Apparatus for the inspection of an article comprising camera means for viewing at least a part of an article to be inspected digitizing means coupled to said camera means for digitizing on a line by line basis at least part of the image of an article to be inspected to provide an array of first data values, each first data value being a digital representation of the intensity of the respective pixel of the image first calculating means coupled to said digitizing means for calculating an array of second data values, each second data value indicating the direction of the intensity gradient for each respective first data value second calculating means coupled to said first calculating means for calculating an array of single third data values, each third data value being related in relative array position to a respective second data value and responsive to the variability of the second data values within he neighborhood of that respective second data value, each neighborhood of each second data value being no larger than 3×3 neighborhood and chosen so that each second data value has the same relative neighborhood location as each other respective second data value has to its neighborhood location, whereby the second image array is transformed into a single third image array, and characterizing means coupled to said second calculating means for characterizing the article being inspected utilizing, at least in part, the third data values.

26. The apparatus of claim 25 wherein said second calculating means is a means for calculating each third data value responsive to the variability of the second data values within a 3×3 neighborhood of that respective second data value.

27. The apparatus of claim 26 wherein the 3×3 neighborhood is a 3×3 pixel neighborhood.

28. The apparatus of claim 26 wherein the 3×3 neighborhood is a 3×3 neighborhood of cells, each cell being an N×N array of pixels having a representative second data value for each cell.

29. In a method of inspection wherein picture elements of an image of an article being inspected are analyzed to characterize the article, the improvement comprising:
(a) determining an array of data values, each data value representing the direction of the local intensity gradient for each picture element;
(b) determining from the direction of the local intensity gradient and as a single data value, the variability of the direction of the local intensity gradient within the neighborhood of each respective picture element, each neighborhood of each picture element being no more than a 3×3 neighborhood and chosen so that each picture element has the same relative neighborhood location as each other picture element has to its neighborhood location; and
(c) characterizing the article being inspected utilizing, at least in part, the variability of the direction of the local intensity gradient within the neighborhood of a plurality of picture elements.

30. A method of inspection of an article comprising steps of
(a) digitizing the image of an article to be inspected to provide an array of first data values, each first data value being a digital representation of the intensity of the respective pixel of the image
(b) calculating an array of second data values, each second data value indicating the direction of the intensity gradient for each respective first data value
(c) calculating an array of third data values, each third data value being related to a respective second data value and responsive to the variability of the second data values within a local group of second data values forming the neighborhood of that respective second data value, each neighborhood of each second data value being chosen so that each second data value has the same relative neighborhood location as each other respective second data value has to its neighborhood location
(d) calculating an array of fourth data values, each fourth data value being responsive to the magnitude of the intensity gradient at the respective image portion as indicated by the array of first data values
(e) multiplying each fourth data value with a respective third data value, and
(f) characterizing the article being inspected by the product of the third and fourth data values.

31. The method of claim 30 wherein the article being inspected is characterized by counting the number of products of the third and fourth data values which are within a predetermined value range.

32. The method of claim 30 wherein at least one of said third and fourth data values are each transformed in a predetermined manner prior to combining respective ones of said third and fourth data values.

33. The method of claim 32 wherein the fourth data values are smoothed prior to combining with the third data values.

34. A method of inspection of an article by analyzing the image thereof comprising steps of
(a) digitizing on a line by line basis at least part of the image of an article to be inspected to provide an array of first data values, each first data value being a digital representative of the intensity of the respective element of the image
(b) calculating an array of second data values, each second data value indicating the direction of the intensity gradient for each respective first data value
(c) calculating an array of third data values, each third data value being related in relative array position to a respective second data value and responsive to the variability of the second data values within the 3×3 neighborhood of that respective second data value, each neighborhood of each second data value being chosen so that each second data value has the same relative neighborhood location as each respective second data value has its neighborhood location, and
(d) characterizing the article being inspected utilizing, at least in part, the third data values,
wherein the 3×3 neighborhood is a 3×3 neighborhood of cells, each cell being an N×N array of pixels having a representative second data value for each cell, and further comprising the step of calculating for each N×N array of second data values a representative second data value, and wherein, in step C, each third data value is responsive to the variability of the representative second data values within each corresponding 3×3 neighborhood of representative second data values.

35. The method of claim 34 wherein each representative second data value is a mean data value.

36. Apparatus for the inspection of an article comprising camera means for viewing at least a part of an article to be inspected digitizing means coupled to said camera means for digitizing on a line by line basis at least in part of the image of an article to be inspected to provide an array of first data values, each first data value being a digital representation of the intensity of the respective pixel of the image first calculating means coupled to said digitizing means for calculating an array of second data values, each second data value indicating the direction of the intensity gradient for each respective first data value second calculating means coupled to said first calculating means for calculating an array of third data values, each third data value being related in relative array position to a respective second data value and responsive to the variability of the second data values within a 3×3 neighborhood of that respective second data value, each neighborhood of each second data value being chosen so that each second data value has the same relative neighborhood location as each other respective second data value has to its neighborhood location, characterizing means coupled to said second calculating means for characterizing the article being inspected utilizing, at least in part, the third data values, wherein the 3×3 neighborhood is a 3×3 neighborhood of cells, each cell being an N×N array of pixels having a representative second data value for each cell, and further comprising third calculating means coupled to said second calculating means for calculating for each N×N array of second data values a representative second data value, and wherein said second calculating means is coupled to said first calculating means through said third calculating means, whereby each third data value is responsive to the variability of the representative second data values within each corresponding 3×3 neighborhood of representative second data values.

37. The apparatus of claim 28 wherein each representative second data value is a mean data value.

* * * * *